(12) United States Patent
Koteles (10) Patent No.: US 10,806,328 B2
(45) Date of Patent: Oct. 20, 2020

(54) EASY-MOUNTING UNIVERSAL STABILIZER ARM CLAMP

(71) Applicant: William J. Koteles, Cleveland, OH (US)

(72) Inventor: William J. Koteles, Cleveland, OH (US)

(73) Assignee: PEMCO, INC., Cleveland, OH (US)

(*) Notice: Subject to any disclaimer, the term of this patent is extended or adjusted under 35 U.S.C. 154(b) by 0 days.

(21) Appl. No.: 16/259,673

(22) Filed: Jan. 28, 2019

(65) Prior Publication Data

US 2019/0231176 A1 Aug. 1, 2019

Related U.S. Application Data

(60) Provisional application No. 62/622,323, filed on Jan. 26, 2018.

(51) Int. Cl.
| | |
|---|---|
| *A61B 1/00* | (2006.01) |
| *F16M 13/02* | (2006.01) |
| *A61B 90/50* | (2016.01) |
| *F16B 2/12* | (2006.01) |
| *A61B 90/57* | (2016.01) |

(52) U.S. Cl.
CPC .......... *A61B 1/00149* (2013.01); *A61B 90/50* (2016.02); *F16M 13/022* (2013.01); *A61B 2090/571* (2016.02); *F16B 2/12* (2013.01); *F16M 2200/022* (2013.01)

(58) Field of Classification Search
CPC ................ A61B 1/00149; A61B 90/50; A61B 2090/571; F16M 13/022; F16M 2200/022; F16B 2/12; F16C 11/06

USPC ................ 248/176.1, 181.1; 403/56, 57, 90; 600/228, 229

See application file for complete search history.

(56) References Cited

U.S. PATENT DOCUMENTS

| | | | | |
|---|---|---|---|---|
| 1,132,554 | A * | 3/1915 | Ah ...................... | B60Q 1/0483 248/229.14 |
| 2,188,701 | A * | 1/1940 | Brullhardt ........... | A47J 43/1012 248/157 |
| 2,586,636 | A * | 2/1952 | Fischer ................. | A01K 97/28 269/4 |
| 2,950,836 | A * | 8/1960 | Murdock ............ | A24F 19/0092 220/576 |
| 3,495,857 | A * | 2/1970 | Hawke ................. | E04B 1/5831 403/57 |
| 6,244,553 | B1 * | 6/2001 | Wang ..................... | B60R 11/02 248/278.1 |

(Continued)

*Primary Examiner* — Nkeisha Smith
(74) *Attorney, Agent, or Firm* — Renner, Otto, Boisselle & Sklar, LLP (57) ABSTRACT

A clamping mechanism for an articulated stabilizer arm includes a body for supporting an articulated stabilizer arm. The body has a bore with a longitudinal axis, and a planar face parallel to the axis of the bore has a clamping surface. The clamping mechanism further includes a clamping plate movable relative to the body, the clamping plate having a planar face with a clamping surface facing the clamping surface of the body. The clamping plate further includes a control post extending from the planar face of the clamping plate inwardly of the circumference of the clamping plate, and configured to move the clamping plate through a range of positions from adjacent to the body and spaced from the body.

8 Claims, 6 Drawing Sheets

(56) References Cited

U.S. PATENT DOCUMENTS

| | | | | |
|---|---|---|---|---|
| 6,588,712 B2 * | 7/2003 | Brell | ............... | F16L 3/1091 248/58 |
| 6,669,155 B2 * | 12/2003 | Ron | ............... | B60R 11/0241 248/176.1 |
| 7,523,904 B2 * | 4/2009 | Carnevali | ............... | F16C 11/10 248/176.1 |
| 7,926,774 B1 * | 4/2011 | Wilson | ............... | F16M 13/00 248/181.1 |
| 8,230,863 B2 * | 7/2012 | Ravikumar | ............... | A61B 90/57 128/845 |
| 8,398,331 B2 * | 3/2013 | Esdaile | ............... | E04H 15/34 403/385 |

* cited by examiner

EASY-MOUNTING UNIVERSAL STABILIZER ARM CLAMP

FIELD OF THE INVENTION

The invention described below relates to surgical support devices, more specifically to articulating, load-bearing flexible stabilizer arms, particularly suited for use as surgical tissue stabilizers used to provide hands-free support during a surgical procedure, and more particularly clamping mechanisms for stabilizer arms mountable on thoracic access devices such as sternotomy retractors.

BACKGROUND

Various surgical devices, including retractors, have been used for many years for lifting, holding, or spreading body parts and surgical incisions. In surgery, it is common practice to mount articulating, load-bearing flexible stabilizer arms as adjustable supporting brackets on a side rail of an operating table to support and position tools, retractors, endoscopes, and other surgical devices.

U.S. Pat. No. 4,949,927, for example, discloses an articulable column and, more particularly, describes prior art columns of the ball and socket type which are flexible in their normal state and which, by application of tension from a central cable, become rigid.

U.S. Pat. No. 5,727,569 teaches that the use of a tissue stabilizer that is attached to the wall of the heart by drawing a vacuum in an array of suction cups. With one or more such devices attached to the wall of the heart, the site at which the repair is to take place can be held fixed while the heart continues to beat.

The tissue stabilizer may be supported using a lockable articulating column, such as disclosed in U.S. Pat. No. 6,860,668. A lockable articulating column is described as a flexible, articulable column having a central tensioning cable strung through a series of ball and socket members. When the cable is tensioned, the column becomes rigid. Releasing the tension returns the column to its flexible state. Thus, flexible stabilizer arms can be fixed into a desired position, released and repositioned as needed.

SUMMARY OF THE INVENTION

The flexibility provided by existing articulated stabilizer arms is not unlimited, however, and the tighter the bend in the articulated arm, the harder it is to hold the arm in the desired position. Applicant recognized that many prior articulated arms could only be clamped perpendicular to the support structure on which they are mounted, and that providing a clamp that could be mounted to a support structure at a greater range of angles would be advantageous in optimizing the curvature of the stabilizer arms. Thus, the present invention provides a solution to this problem by providing a wider, circumferential clamping mechanism that permits greater latitude in the orientation of the stabilizer arm, providing an position-adjustable articulated stabilizer arm that facilitates fixing the stabilizer arm in a desired position with more gradual bending of the stabilizer arm.

Thus, in one embodiment, the present invention provides a clamping mechanism for an articulated stabilizer arm that includes a body for supporting an articulated stabilizer arm, and a clamping plate movable relative to the body. The body has a bore with a longitudinal axis, and a planar face parallel to the axis of the bore that has a clamping surface. In turn, the clamping plate has a planar face with a clamping surface facing the clamping surface of the body. The clamping plate further includes a control post extending from the planar face of the clamping plate inwardly of the circumference of the clamping plate, and configured to move the clamping plate through a range of positions from adjacent to the body and spaced from the body.

The clamping plate may further include at least one guide rod extending parallel to the control post and closely received in a corresponding guide passage in the body.

Thus, the present invention provides an elegant solution to the problems encountered in the prior art, as will be more fully appreciated based on the following description of various embodiments of the present invention.

BRIEF DESCRIPTION OF THE DRAWINGS

The present invention may be useful with a variety of retractor apparatus. The annexed drawings are intended to provide an exemplary, non-limiting depiction of a suitable spreadable retractor apparatus and to demonstrate the disclosed invention; for the purpose of providing a better understanding of the invention; and are not intended to be limiting in any way.

For simplicity and clarity of illustration, elements shown in the Figures have not necessarily been drawn to scale. For example, the dimensions of some of the elements may be exaggerated relative to each other for clarity. Further, where considered appropriate, reference numerals may be repeated among the Figures to indicate corresponding elements.

DETAILED DESCRIPTION

Figure 1:
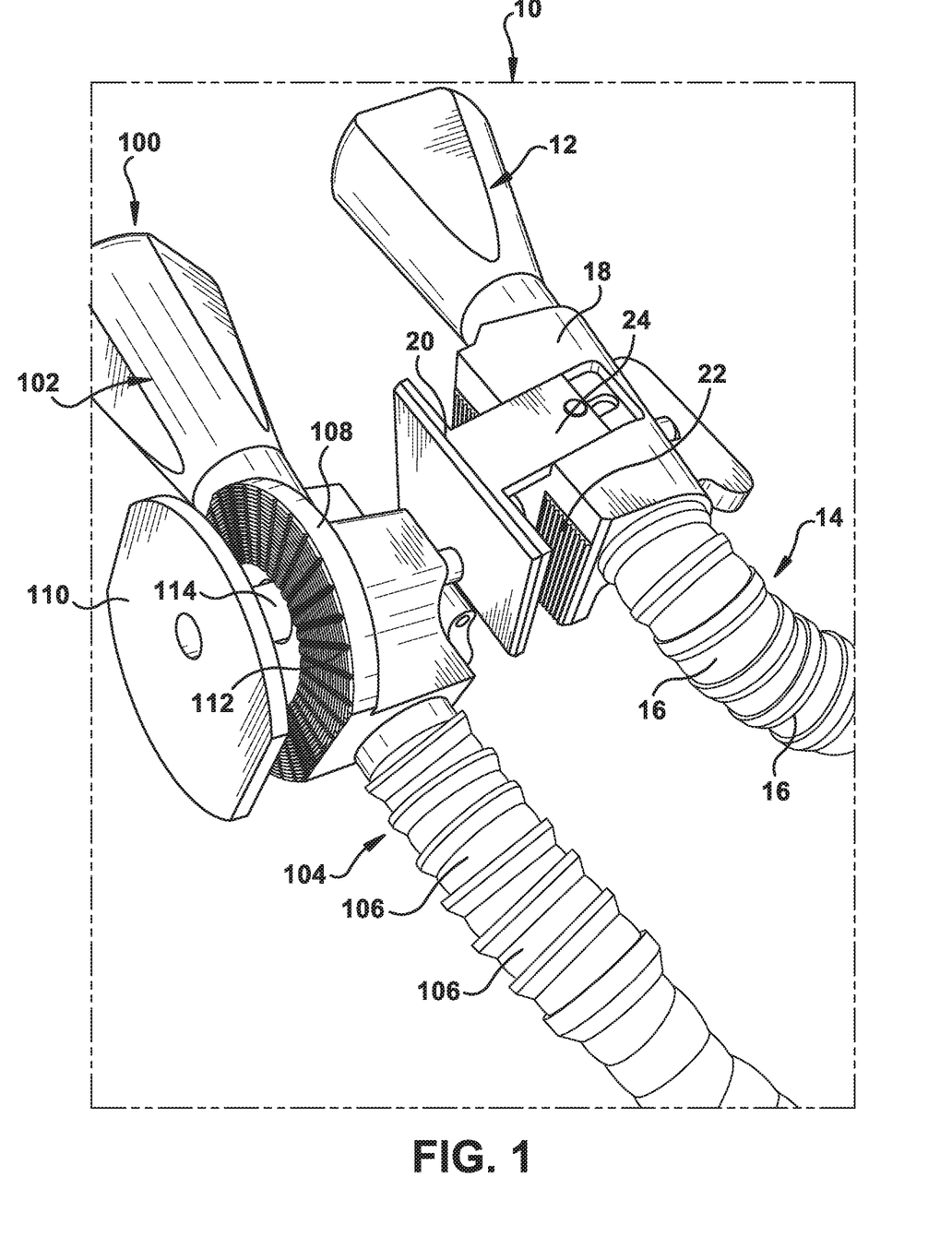
FIG. 1 is a side perspective view of a clamping mechanism for an articulated stabilizer arm provided by the invention on the left, and a prior art clamping mechanism for an articulated stabilizer arm on the right.
Figure 2:
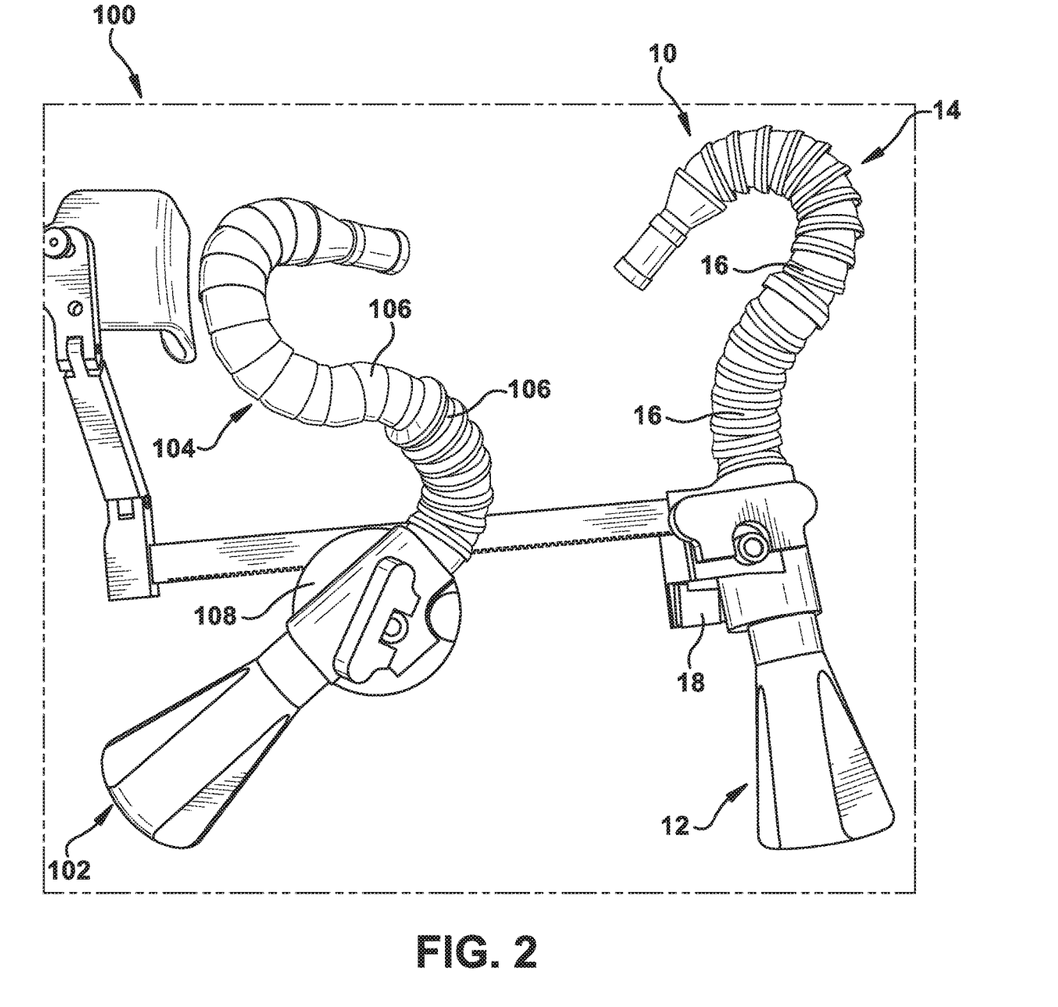
FIG. 2 is a top perspective view of a clamping mechanism for an articulated stabilizer arm provided by the invention on the left, and a prior art clamping mechanism for an articulated stabilizer arm on the right, both mounted on a surgical spreader.
Figure 3:
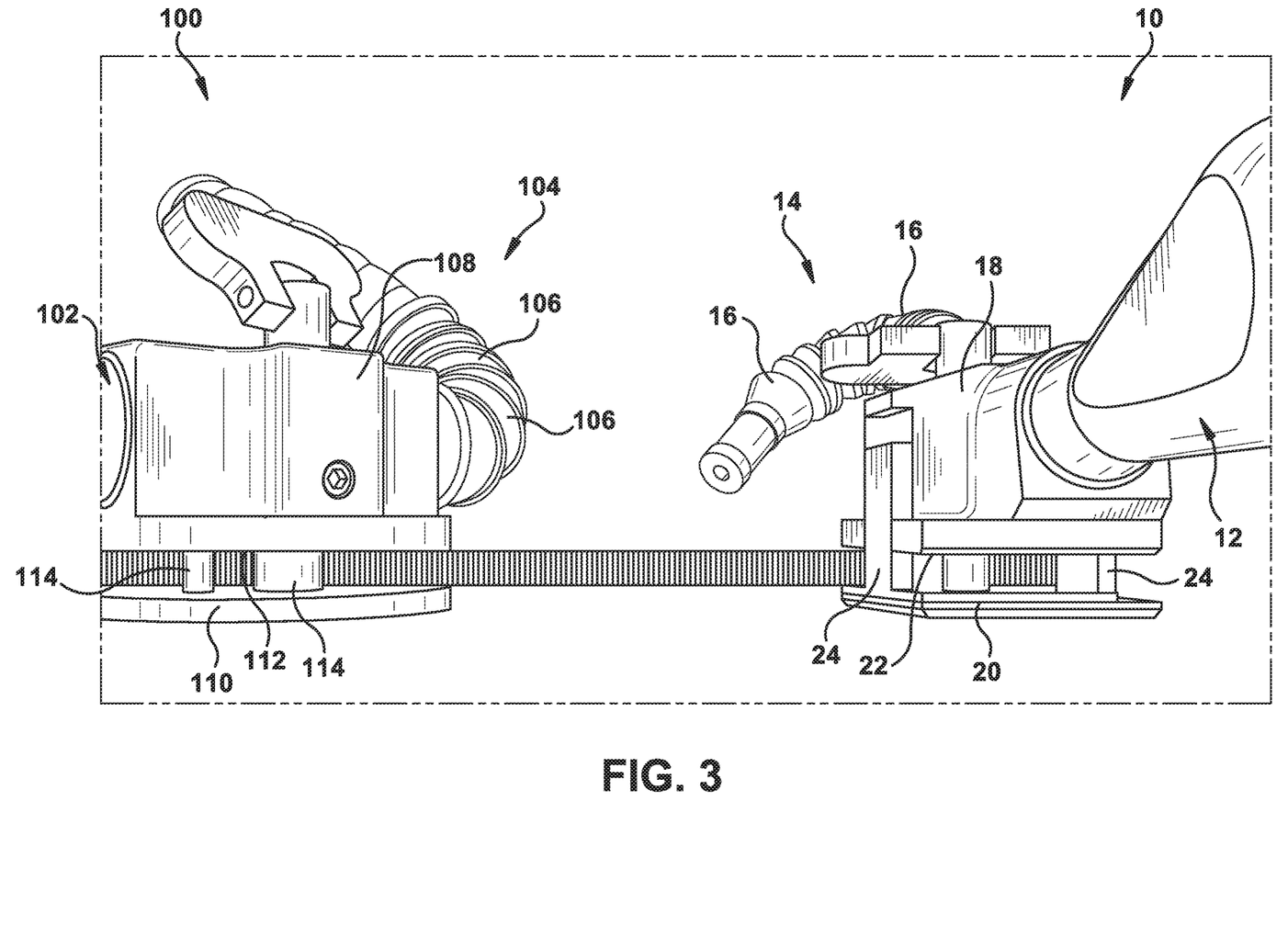
FIG. 3 is an end perspective view looking ninety degrees from FIG. 2.

The present invention provides a clamping mechanism for an articulated stabilizer arm that can be mounted to a support structure to direct the articulated arm in any direction. For comparison purposes, an exemplary clamping mechanism 100 provided by the invention is shown in FIGS. 1 to 3 on the left, with a prior art clamping mechanism 10 shown on the right. Some differences and similarities are readily apparent.

Both devices appear to have some similar or identical components, such as a tensioning handle 102 and 12, and the parts that make up the articulated stabilizer arm 104 and 14. Those parts include a plurality of articulating elements 106 and 16 aligned end-to-end and a cable (not shown) coupled to the tensioning handle 102 and 12 and extending through an interior passage in the articulating elements 106 and 16. Turning the tensioning handle 102 and 12 advances or retracts the cable to fix those articulating elements 106 and 16 in position or loosen them for repositioning. Similar articulated stabilizer arms 104 and 14 are known.

Additionally, while both devices include a clamping mechanism 10 and 20 having both a clamping body 108 and 18 and a clamping plate 110 and 20, there are obvious differences between them. As will be further explained below, the clamping body 108 of the present invention has a bore (not shown), through which the tensioning cable (not shown) passes, and the bore has an axis that is parallel to a clamping surface 112 of that body 108. In contrast, the prior art clamping body 18 has a bore (not shown) that is angled slightly relative to its clamping surface 22. As shown, the axis of the bore is generally aligned with an axis of the respective tensioning handle 102 and 12. The tensioning handle 12 is rotatable about an axis that is inclined downwardly from a distal end of the tensioning handle 12 to the body 18, whereas the tensioning handle 102 rotates about an axis that is approximately parallel to the clamping surface 112 of the body 108. This arrangement in the prior art clamping device 10 may be advantageous for directing the articulating elements 16 to extend downward toward a patient during surgery, but can make it difficult to access the lower side of the bore, and could make positioning the clamping mechanism 10 relative to other surgical instruments or support structures more difficult. If the clamping body 10 were to rotate about such an inclined plane, the tensioning handle 12 could be on the lower end and extend toward the patient, further complicating tensioning and releasing the articulating elements 16.

In addition, the elements that control and guide movement of the clamping plate 110 and 20 relative to the respective body 108 and 18 are different. In the prior art clamping mechanism 10, guide elements 24 for the clamping plate 20 are on the outside, preventing that side of the clamping plate 20 from engaging any support structure. Thus only two sides of the prior art clamping plate 20 are potentially available for clamping to a support. In contrast, the clamping mechanism 100 provided by the present invention recesses the guide elements 114 inwardly relative to the periphery of the clamping surface 112, enabling engagement with a support from any side.

Figure 4:
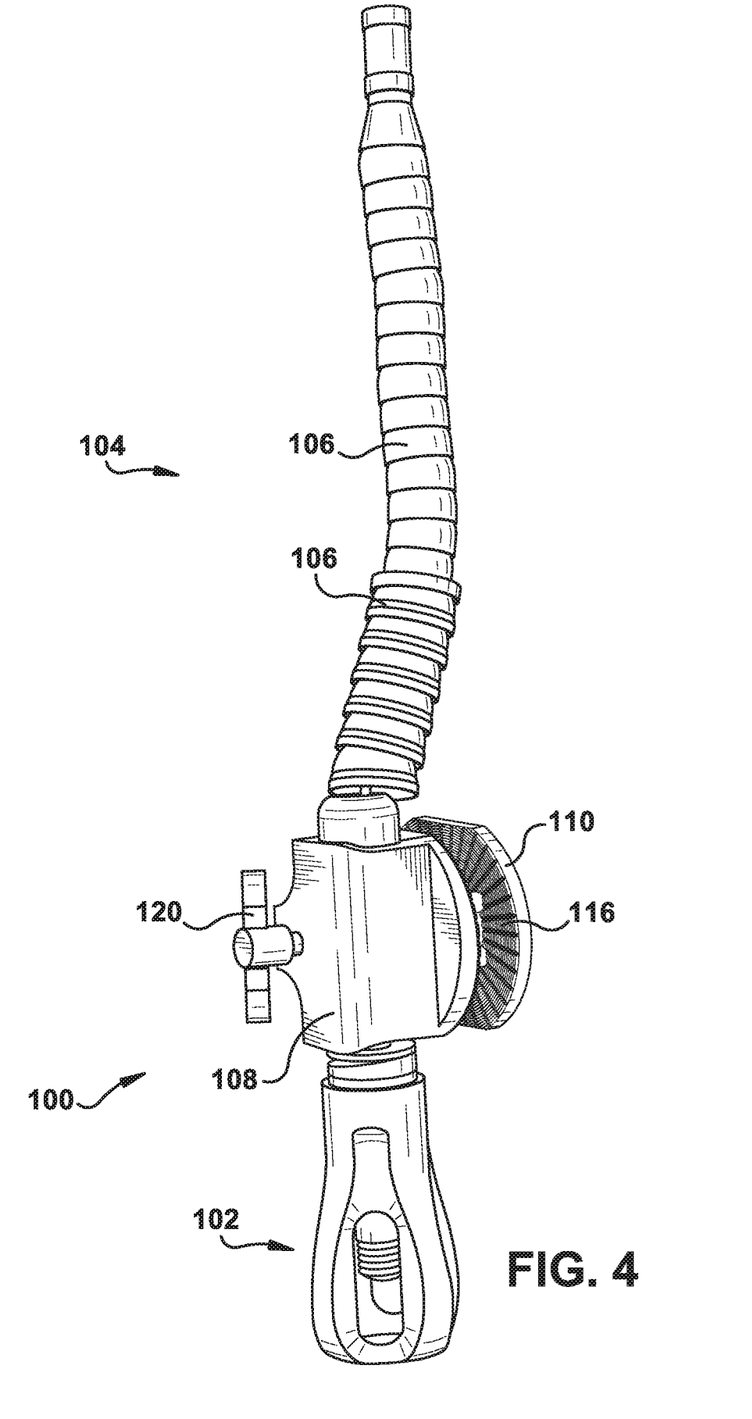
FIG. 4 is a side perspective view of a clamping mechanism of an articulated stabilizer arm provided by the invention.
Figure 5:
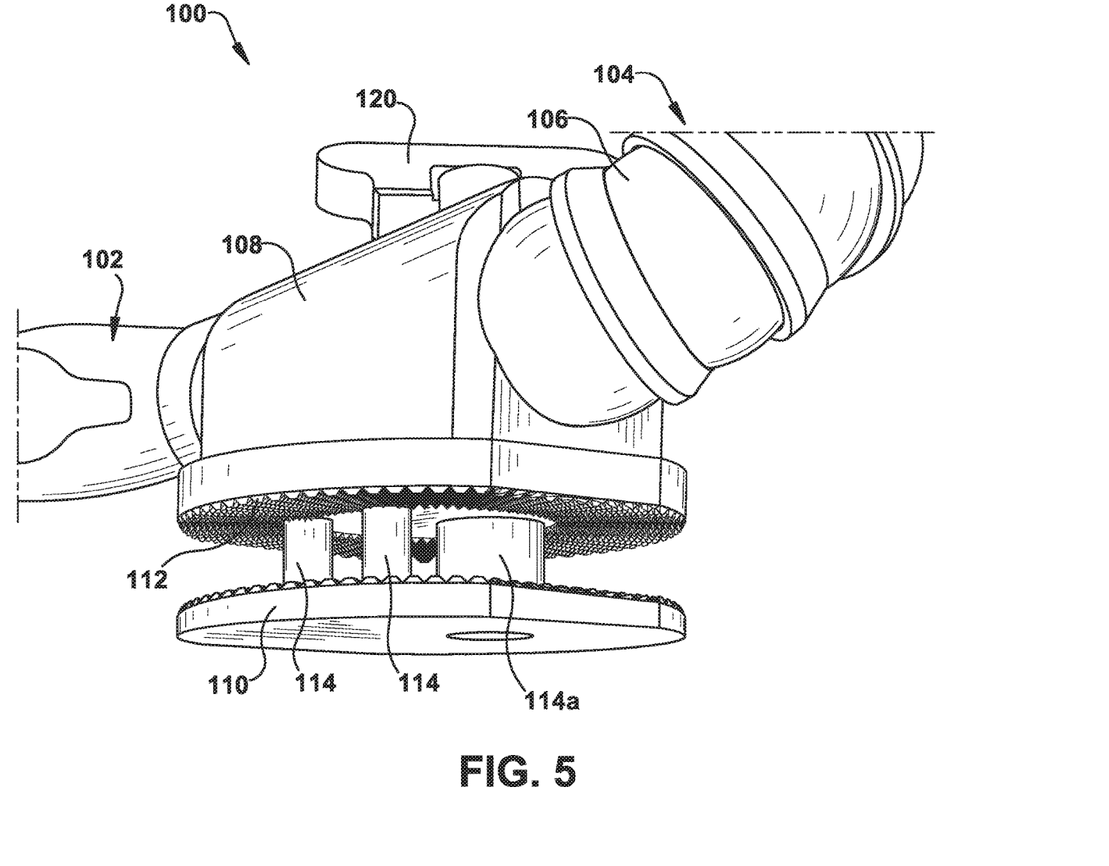
FIG. 5 is a side perspective view of the clamping mechanism of FIG. 4.
Figure 6:
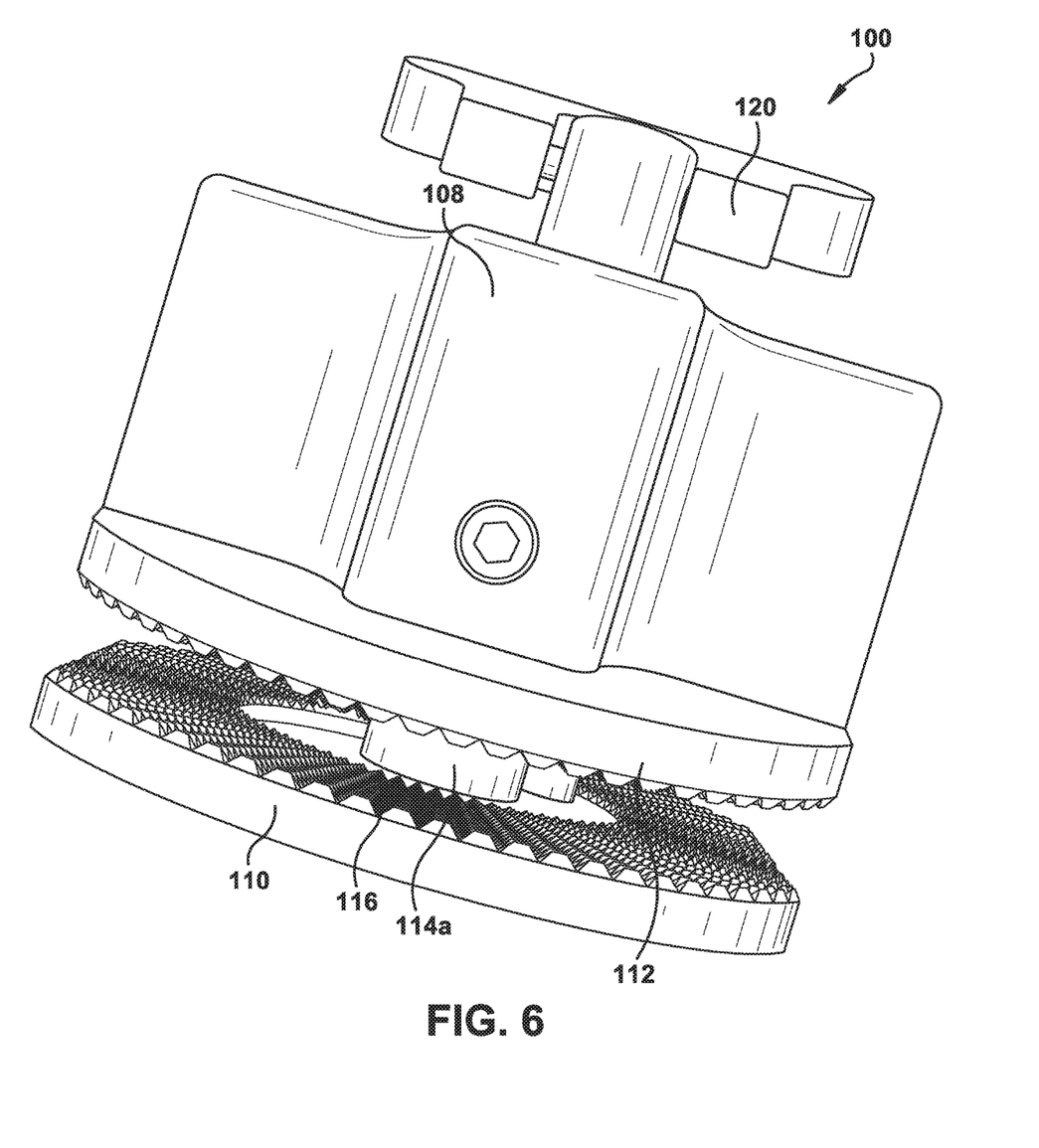
FIG. 6 is an end perspective view of the clamping mechanism of FIG. 4.

Turning now to FIGS. 4 to 6, an exemplary clamping mechanism 100 provided by the invention is shown. The clamping mechanism 100 includes a body 108 for supporting an articulated stabilizer arm 104 and a clamping plate 110 movable relative to the body 108. The body 108 has a bore with a longitudinal axis, and a planar face parallel to the axis of the bore that includes a clamping surface 112. Accordingly, when the clamping mechanism 100 is mounted on a horizontal support structure, the respective clamping surfaces of the body 108 and the clamping plate 110 will be parallel and horizontal, and the bore of the clamping mechanism 100 also will be horizontal. Thus, the tensioning handle 102 and the articulated stabilizer arm 104 also will extend horizontally from the body 108, making it easier to minimize the likelihood of interference with the patient or other surgical instruments.

The clamping plate 110 has a planar face with a clamping surface 116 facing, and generally parallel to, the clamping surface 112 of the body 108. The clamping plate 110 also includes a control post 114 extending from the planar face of the clamping plate 110 inwardly of the circumference of the clamping plate 110, and configured to move the clamping plate 110 through a range of positions from adjacent to the body 108 and spaced from the body 108.

The respective clamping surfaces 112 and 116 of the base 108 and the clamping plate 110, respectively, may be adjacent an outer periphery of the respective surfaces.

The respective clamping surfaces 112 and 116 of the base 108 and the clamping plate 110, respectively, typically have surface textures configured to increase friction under clamping pressure, such as grooves, ridges, knurling, or other surface treatments that increase friction.

The body 108 and the clamping plate 110 may be made of stainless steel, particularly surgical grade stainless steel, or any other material suitable for use as a medical device.

The clamping mechanism 100 may further include a threaded member (not shown) for moving and locking the clamping plate 110 in place relative to the body 108. The body 108 includes a passage therethrough aligned with a centrally-located control post 114a on the clamping plate 110, and the threaded member is configured to cooperate with the control post 114a to vary the position of the clamping plate 110 relative to the body 108. A handle 120 may be provided to turn the threaded member relative to the control post 114a.

The clamping plate 110 also may include at least one guide rod 114 extending parallel to the control post 114a and closely received in a corresponding guide passage in the body 108 to help guide the movement of the clamping plate 110 and maintain a parallel relationship between the respective clamping surfaces 112 and 116. The illustrated embodiment includes two guide rods 114, further ensuring parallel movement between the respective clamping surfaces 112 and 116 of the body 108 and the clamping plate 110, respectively.

An exemplary articulated stabilizer arm is described in U.S. Pat. No. 6,860,668, which is incorporated herein in its entirety. Such a stabilizer arm 104 may be used in connection with the body 108 provided by the present invention.

In summary, the present invention provides a clamping mechanism 100 for an articulated stabilizer arm 104 that includes a body 108 for supporting an articulated stabilizer arm 104 and a clamping plate 110 movable relative to the body 108. The body 108 has a bore with a longitudinal axis, and a planar face parallel to the axis of the bore has a clamping surface 112. The clamping plate 110 has a planar face with a clamping surface 116 facing the clamping surface 112 of the body 108. The clamping plate 110 further includes a control post 114a extending from the planar face of the clamping plate 110 inwardly of the circumference of the clamping plate 110, and configured to move the clamping plate 110 through a range of positions from adjacent to the body 108 and spaced from the body 108.

While the principles of the invention have been explained in relation to certain particular embodiments, these embodiments are provided for purposes of illustration. It is to be understood that various modifications thereof will become apparent to those skilled in the art upon reading the specification. Therefore, it is to be understood that the invention disclosed herein is intended to cover such modifications as fall within the scope of the appended claims. The scope of the invention is limited only by the scope of the claims.

The invention claimed is:

1. A clamping mechanism for an articulated stabilizer arm, comprising:
   a body for supporting an articulated stabilizer arm, the body having a bore with a longitudinal axis, and a first planar face parallel to the axis of the bore having a first clamping surface; and
   a clamping plate movable relative to the body, the clamping plate having a second planar face with a second clamping surface facing the first clamping surface of the body, the second clamping surface of the clamping plate being parallel to the first clamping surface of the body, the clamping plate further including a control post extending from the second planar face of the second clamping plate inwardly of a circumference of the second clamping plate, and configured to move the second clamping plate through a range of positions from adjacent to the body and spaced from the body while maintaining the second clamping surface parallel to the first clamping surface;

wherein the clamping plate further includes at least one guide rod extending parallel to the control post and closely received in a corresponding guide passage in the body.

2. A clamping mechanism for an articulated stabilizer arm as set forth in claim 1, wherein the first clamping surface of the body is adjacent an outer periphery of the first planar face and the second clamping surface of the clamping plate is adjacent an outer periphery of the second planar face of the clamping plate.

3. A clamping mechanism for an articulated stabilizer arm as set forth in claim 1, wherein the first clamping surface of the body and the second clamping surface of the clamping plate have surface textures configured to increase friction under clamping pressure.

4. A clamping mechanism for an articulated stabilizer arm as set forth in claim 1, wherein the body and the clamping plate are made of stainless steel.

5. A clamping mechanism for an articulated stabilizer arm, comprising comprising:
- a body for supporting an articulated stabilizer arm, the body having a bore with a longitudinal axis, and a first planar face parallel to the axis of the bore having a first clamping surface;
- a clamping plate movable relative to the body, the clamping plate having a second planar face with a second clamping surface facing the first clamping surface of the body, the second clamping surface of the clamping plate being parallel to the first clamping surface of the body, the clamping plate further including a control post extending from the second planar face of the second clamping plate inwardly of a circumference of the second clamping plate, and configured to move the second clamping plate through a range of positions from adjacent to the body and spaced from the body while maintaining the second clamping surface parallel to the first clamping surface; and
- a threaded member, the body including a passage therethrough aligned with the control post on the clamping plate, and the threaded member is configured to cooperate with the control post to vary the position of the clamping plate relative to the body.

6. A clamping mechanism for an articulated stabilizer arm as set forth in claim 5, wherein the first clamping surface of the body is adjacent an outer periphery of the first planar face and the second clamping surface of the clamping plate is adjacent an outer periphery of the second planar face of the clamping plate.

7. A clamping mechanism for an articulated stabilizer arm as set forth in claim 5, wherein the first clamping surface of the body and the second clamping surface of the clamping plate have surface textures configured to increase friction under clamping pressure.

8. A clamping mechanism for an articulated stabilizer arm as set forth in claim 5, wherein the body and the clamping plate are made of stainless steel.

* * * * *